United States Patent [19]

Christianson et al.

[11] Patent Number: 4,548,901
[45] Date of Patent: Oct. 22, 1985

[54] PLANTLET GENERATION BY CELL CULTURE

[75] Inventors: Michael L. Christianson, San Francisco; Debra A. Warnick, Palo Alto, both of Calif.; Peter S. Carlson, Washington, D.C.

[73] Assignee: Zoecon Corporation, Palo Alto, Calif.

[21] Appl. No.: 506,476

[22] Filed: Jun. 21, 1983

[51] Int. Cl.⁴ ............................................. A01G 1/00
[52] U.S. Cl. ..................................... 435/241; 47/58
[58] Field of Search .................... 47/58; 435/240–241

[56] References Cited
PUBLICATIONS

Morphogenetic Studies..., Yeoman, et al., 1982, Cambridge Press, pp. 231–251.

Primary Examiner—Robert E. Bagwill
Attorney, Agent, or Firm—Hana Dolezalova; Jacqueline S. Larson

[57] ABSTRACT

Plantlet generation by cell culture wherein a morphogenetically competent cell suspension culture is prepared which can be maintained by serial subculture. Transfer of aggregates of the suspension culture to an expression medium produces, after a few days, well formed bipolar embryoids which undergo shoot development and subsequent rooting to complete plantlet development.

16 Claims, No Drawings

PLANTLET GENERATION BY CELL CULTURE

The present invention relates to plantlet generation by cell culture. More specifically, this invention relates to a method for plantlet generation which includes the preparation of a novel morphogenetically competent cell suspension culture, the preparation of bipolar embryoids, and novel media for practice of the invention. A principal advantage is that the suspension culture of this invention can be maintained by serial subculture and thereby provide an ongoing source of cell aggregates which are morphogenetically competent and capable of developing into bipolar embryoids. The bipolar embryoids are capable of completing plantlet development.

Plantlets can be produced from tissue or cell culture by the organogenic or embryogenic process. An excellent description of the two processes, influences of exogeneous auxins (growth regulators), matters of terminology, and list of references is provided by G. G. Henshaw et al., "Morphogenetic Studies in Plant Tissue Cultures," pp. 231–251, in M. M. Yeoman and D. E. S. Truman, eds., "Differentiation in vitro," Cambridge Press (1982).

The route of plantlet production from cell cultures with which the present invention is concerned is the embryogenic route. In this route a group of cells become organized into a bipolar embryoid which subsequently will develop bud primordia at one end and root primordia at the other end. This route to the generation of plantlets by embryogenesis may employ suspension culture wherein the cells are suspended in a gently agitated liquid medium. Certain cells from the suspension can be used to produce embryoids.

Plantlet generation by embryogenesis using suspension culture has been successfully employed for the legume alfalfa by K. A. Walker and S. J. Sato, *Plant Cell Tissue Organ Culture*, 1, 109–121 (1981). The authors discuss the effects and the interaction of media, ammonium ion, nitrate anion and exogenous auxin on morphogenesis. It was observed that no embryogenesis occurred in the absence of either ammonium or nitrate. In the case of large-seeded legumes, generation of plantlets by embryogenesis has not been reported. G. C. Phillips and G. B. Collins, ibid, 1, 123–129 (1981) describe experiments in the induction and development of embryoids from cell cultures of soybean. The objective of the experiments to generate soybean plantlets was not achieved. The experiments advanced to the formation of a shoot structure which, however, did not develop into a plantlet.

In accordance with the present invention, there is provided a method for plantlet generation by the process of embryogenesis comprising the preparation of a morphogenetically competent cell suspension culture. The method of the present invention is applicable to the generation of plantlets of large-seeded legumes such as soybeans of the genus Glycine and peas of the genus Pisum. The embryoids produced from the suspension culture are capable of completing plantlet development. The suspension can be maintained by serial subculture.

In the practice of the present invention, explants of the plant to be regenerated are cultured and by recurrent selection in a culture regime involving the coordinate change of exogenous auxin and nitrogen source, organized cells in the form of an aggregate is produced which is morphogenetically competent. For purposes of illustration of the practice of the invention, a specific embodiment relating to embryogenic generation of a soybean plant, *Glycine max* cv Mitchell, is described.

In the practice of the specific embodiment described in detail hereinafter, explants to initiate callus are taken from young embryos of the soybean. The embryos are removed aseptically from 2.5 to 3.0 cm pods of plants grown in a greenhouse under natural photoperiod. Suitable aseptic procedures are described by Phillips and Collins, supra. Explants are prepared from the embryo axis by cutting into about 1 to 2 mm pieces. The thus-obtained explants are then used to initiate callus by culturing in a basal medium (herein "Medium A") which is prepared by the procedure of T. Murashige and F. Skoog, *Physiol. Plant.*, 15, 473 (1962). Medium A contains exogenous auxin within the range of about 2 mg/l to 8 mg/l. In the detailed example hereinafter, there is used 5 mg/l of the auxin 2,4-dichlorophenoxyacetic acid. The particular auxin or mixture of auxins used in Medium A and the most advantageous concentration thereof may be established by routine experimentation. Medium A may be in solid form as, for example, through the use of solidification of the medium by the addition of agar. Medium A has a near neutral pH of about 6.0; a pH within the range of about 4.5 to 7.5 should be satisfactory. The explants are cultured in Medium A and observed for the formation of callus and transition of the callus into apparently organized cells. After a period of time, hard, non-friable tissue (embryo-like structures), herein called "cultured explants" are visually selected for transfer to a new culture medium. In one embodiment, culturing of the explants in Medium A was continued for about 18 days and then selection of and transfer of cultured explants to Medium A again wherein the culturing period ran for about 40 days. Then, the process of selection of cultured explants was repeated and the selected cultured explants transferred to a new Medium B. Medium B is similar to Medium A with the difference that the concentration and activity level of the auxin is substantially reduced. As illustrated in the specific example, there was used the auxin indole-3-acetic acid (IAA) which must be used in larger amounts than 2,4-dichloro-phenoxyacetic acid (2,4-D) in order to obtain an equivalent plant growth regulator dose/response-activity level. The culturing in Medium B is observed and allowed to continue, for example, for a period of about 90 days. Selected cultured explants are then removed from Medium B and transferred for further culturing in Medium A for, for example, a period of about 40 days. Then, cultured explants are selected from Medium A which are transferred to a new medium. The new medium, Medium C, differs from Medium A in that the nitrogen source in Medium A is replaced by an ammonium salt and Medium C is free of nitrate anion. This change in culture medium, i.e., Medium C, wherein ammonium ion is the sole nitrogen source in the culture is essential in the generation of a morphogenetically competent cell culture. If, instead of Medium C there is used Medium A, there is subsequently generated green structures but not a single bipolar embryoid which demonstrates the loss of morphogenetic competence of the cell culture. Culturing in Medium C is allowed to continue for a period of about 40 days and then selected cultured explants are transferred to a new preparation of Medium A where culturing is continued for about two months. Then, visually selected cultured explants are transferred to (1) an aqueous liquid Medium C and maintained in suspension with mild agitation, herein "Medium D," and (2) an expression medium, herein "Medium E," prepared according to the procedure of T. Y. Cheng et al., *Plant Sci. Lett.*, 19, 91 (1980). The aforementioned selected cultured explants transferred from Medium A to (1) and (2) may be characterized as hard, green, glossy tissue structure covered with small embryoids and are referred to herein as an "aggregate" or "organized callus." The aggregates transferred to Medium D proliferated and gave rise to nodular aggregates of cells in suspension. The suspension culture can be maintained by serial subculture in Medium D. The suspension culture retains the morphogenetically competent ability to form bipolar embryoids in the expression medium which is proven, in subsequent steps, by generation of plantlets. The selected aggregates which were transferred directly to expression medium, Medium E, in (2) above, gave rise to plantlets, each with several elongating internodes.

Plantlet regeneration has been a major stumbling block for the application of genetic engineering or cell culture techniques for both the improvement of plants as a crop and for the study of the plant's basic biology. The present invention removes that block for in vitro selections.

The terminology used herein is not intended to vary from the terminology generally used in the field. However, the meaning of some terms used in the field are not necessarily uniform. Cf. Henshaw et al., supra.

"Plantlet" is a plant asexually reproduced by cell culture.

"Explant" is a section or piece of tissue taken from a plant for culturing.

"Auxin" is a growth regulator that affects the growth of plants.

"Callus" is an unorganized group of cells (formed in response to a cut, severing or injury of a plant).

"Morphogenetically competent" means having the propensity to respond to inductive conditions; the response is morphogenesis, the elaboration of organized tissue or organs.

"Embryoid" means a structure similar in appearance to a plant embryo, a young sporophyte.

The term "ammonium salts," as used herein, means an ammonium salt formed by the ammonium ion and an anion such as chloride, sulfate, carbonate, hydroxide, phosphate citrate or acetate. The term ammonium salts excludes ammonium nitrate.

The term "auxin," as used herein, means a plant growth regulator such as indole-3-acetic acid, indole-3-butyric acid, -4-dichlorophenoxyacetic acid, naphthaleneacetic acid and the like.

The following examples are provided for the purpose of illustrating the practice of the present invention.

Abbreviations:
IAA = indole-3-acetic acid
IBA = indole-3-butyric acid
BA = 6-benzylaminopurine
2ip = 6-dimethylallylaminopurine
2,4-D = 2,4-dichlorophenoxyacetic acid

| PREPARATION OF STOCK SOLUTIONS | |
|---|---|
| Stock Solution A (M & S Major) | 10X Solution (grams) |
| $NH_4NO_3$ | 16.5 |
| $KNO_3$ | 19.0 |
| $CaCl_2.2H_2O$ | 4.4 |
| $MgSo_4.7H_2O$ | 3.7 |
| $KH_2PO_4$ | 1.7 |
| $H_2O$ to 1.0 liter | |
| Stock Solution B (M & S Minor) | 100X Solution (Milligrams) |
| $H_3BO_3$ | 620.0 |
| $MnSO_4.H_2O$ | 1680.0 |
| $ZnSO_4.7H_2O$ | 1060.0 |
| KI | 83.0 |
| $Na_2MoO_4.2H_2O$ | 25.0 |
| $CuSO_4.5H_2O$ | 2.5 |
| $CoCl_2.6H_2O$ | 2.5 |
| $H_2O$ to 1.0 liter | |
| Stock Solution C $Na_2EDTA$ | 1.865 gm in 500 ml $H_2O$ |
| Stock Solution D $FeSO_4.7H_2O$ | 1.390 gm in 500 ml $H_2O$ |

Formulation A, below, was prepared for addition of auxins, sucrose, and the like to obtain the media.

| Formulation A Stock Solution | (milliliters) |
|---|---|
| A | 100.0 |
| B | 10.0 |
| C | 10.0 |
| D | 10.0 |

Culture media were prepared using Formulation A and the listed additives as follows:

| | Medium | | |
|---|---|---|---|
| Culture Media | A | B | E |
| Nicotinic acid, mg/l | 0.5 | 0.5 | 0.5 |
| Pyridoxine.HCl, mg/l | 0.5 | 0.5 | 0.5 |
| Thiamine.HCl, mg/l | 10.0 | 10.0 | 10.0 |
| Inositol, mg/l | 100.0 | 100.0 | 100.0 |
| Sucrose, gm/l | 20.0 | 20.0 | 20.0 |
| 2,4-D, mg/l | 5.0 | — | — |
| IAA, mg/l | — | 2.0 | — |
| 2-ip, mg/l | — | 0.2 | — |
| IBA | — | — | 0.005 |
| BA | — | — | 0.20 |
| $H_2O$ to dilute to 1.0 liter | | | |

Media A, B and E include 130 ml of Formulation A.

EXAMPLE 1

Part A

Aseptically prepared explants (5–10) of the embryo axis of the soybean, *Glycine max* cv Mitchell, were cultured on agar plates using Medium A (about 15–20 ml), solidified with agar (about 9.0 gm/l Difco Bacto-Agar). The pH of the medium was 6.0 prior to and 5.4 after autoclaving. The plates (30) were maintained under constant artificial light (about 300 ft. candles) at room temperature of about 27°.

After a culturing period of 18 days, the cultured explants characterized as hard, non-friable and glossy were selected and transferred to a medium of freshly prepared Medium A and cultured, under same conditions, for a period of 40 days.

Part B

Cultured explants obtained in Part A were then transferred to Medium B which has a much lower activity level of auxin than is present in Medium A. Also, Medium B has 0.2 mg/l of 6-dimethylallylaminopurine (2 ip), a cytokin, whereas Medium A has no exogenous cytokin. Medium B was solidified as in Part A with agar. After a culturing period of about 80 days, same conditions as Part A, selected cultured explants are removed and transferred to a fresh preparation of Medium A and allowed to culture for a period of about 29 days.

Part C

Selected cultured explants obtained in Part B were then transferred to Medium C for a culturing period of about 38 days. Medium C was identical to Medium A except that the ammonium nitrate and potassium nitrate were omitted and 20 millimoles of dibasic ammonium citrate were used in lieu thereof. After culturing, same conditions as Part A, selected cultured explants were transferred to freshly prepared Medium A, solidified and cultured under same conditions as in Part A for a period of about 60 days.

Part D (1) From the cultured explants obtained from Part C, there was selected a cultured explant (hard, glossy, green, non-friable and having small embryoids) which was divided. One-half of the selected cultured explant was transferred to an aqueous liquid Medium D (about 50 ml) to form a suspension. Medium D was contained in a flask and gently rotated at about 125 rpm. Culturing conditions and pH, the same as in Part A. Medium D was identical with Medium C minus agar. The cultured explants (aggregates) in Medium D proliferated and gave rise to nodular aggregates in suspension. The thus-obtained suspension culture can be maintained by serial subculture.

(2) The other one-half of the selected cultured explant from Medium C was transferred to Medium E (expression medium) prepared according to T. Y. Cheng et al., supra. It should be noted that this expression medium represents a change in nitrogen source and a change in auxin. The expression medium is the same as Medium A except that 2,4-D is omitted from Medium A and IBA and BA are added. Two weeks after transfer to the expression medium, the culture contains many well-formed bipolar embryoids. These are often found in clusters attached by the tips of their radicles. The embryoids undergo precocious shoot development and give rise to plantlets, each showing trifoliate leaves and several elongating internodes. The plantlets were transferred to rooting medium at this stage for growth in the greenhouse. Root formation is accomplished in a basal medium plus IAA (same as Medium A except that 0.1 mg/l of IAA is used in place of 2,4-D).

In Medium D, as in Medium C, it is to be noted that the sole source of nitrogen in the salts of the stock solution is ammonium citrate and that no nitrate anion is present. The amount of ammonium citrate or other "ammonium salt," as used herein, was 20 mM. It has been found satisfactory to use from about 20 to 40 mM of ammonium salt; however, lower or higher amounts may be used without departing from the spirit of the invention.

EXAMPLE 2

Cultured explants (aggregates) from the suspension culture prepared in Example 1, Part D(1), were selected and transferred to expression Medium E. About two weeks after transfer, well-formed bipolar embryoids were obtained which developed shoots and were subsequently rooted. Thus, the culture suspension does retain the ability to form embryoids and thereby provides an ongoing source of morphogenetically competent cells of the parent culture for plantlet regeneration.

EXAMPLE 3

The procedure of Example 2 was repeated except that the aggregates were transferred to a Medium F for expression. Culturing the aggregates in Medium F did not result in embryoid formation and development. Medium F is the same medium as Medium C except that the 2,4-D is replaced by 0.005 mg/l IBA plus 0.2 mg/l BA. Thus, the change in the expression medium tested in this example is the nitrogen source as compared to Example 2. It demonstrates that change in auxin alone is not sufficient to trigger complete somatic embryogenesis in the competent cultures of Example 1, Part D (1).

In the descriptions hereinabove, the pH of the culture media and the temperature and light conditions used during culturing were the same as described in Example 1, Part A.

While the invention has been described in detail in connection with a specific embodiment thereof, it will be understood that it is capable of further modifications and this application and appended claims is intended to cover any variations, uses or adaptations of the invention following the principles of the invention and including such departures from the present disclosure as come within known or customary practice within the art.

What is claimed is:

1. A method for generating legume bipolar embryoids which comprises the steps of:
    (a) culturing explants of the legume embryo in a basal medium containing exogenous auxin;
    (b) culturing of the cultured explants obtained in (a) in a basal medium containing exogenous auxin in a lower concentration than in (a);
    (c) culturing of the cultured explants obtained in (b) in a basal medium containing exogenous auxin and an ammonium salt, said medium being free of nitrate anion;
    (d) transfer of the cultured explants obtained in (c) into an aqueous liquid suspension medium containing exogenous auxin and an ammonium salt, said medium being free of nitrate anion, and mildly agitating the medium so as to maintain the cultured explants in suspension; and
    (e) transfer of an aggregate of cells obtained in suspension in (d) to an expression medium containing exogenous auxin and allowing said aggregate to form a bipolar embryoid.

2. The method of Claim 1 wherein the basal medium is in solid form and the explants of step (a) are explants of the embryo axis.

3. The method of Claim 2 wherein the auxins are selected from indole-3-acetic acid, indole-3-butyric acid, napthaleneacetic acid, 2,4-dichlorophenoxyacetic acid, and mixtures thereof.

4. The method of claim 3 wherein the auxin is 2,4-dichlorophenoxyacetic acid.

5. The method of claim 3 wherein the auxin in step (b) is indole-3-acetic acid.

6. The method of claim 2 wherein the ammonium salt is ammonium citrate.

7. The method of claim 1 including the additional step of transferring the embryoid onto a growth medium for development of a plantlet.

8. In a method for producing a morphogenetically competent plantlet regeneration culture wherein explants of a large-seeded legume plant are successively cultured and selectively transferred, the improvement wherein a cultured explant is cultured in a medium containing exogenous auxin and ammonium salt, said medium being free of nitrate anion.

9. The improvement of claim 8 wherein the ammonium salt is the sole source of nitrogen in the medium.

10. The improvement of claim 9 wherein the plant is a legume of the genus Glycine.

11. The improvement of claim 10 wherein the plantlet regeneration culture is an aqueous suspension culture.

12. The improvement of claim 9 wherein the plant is a legume of the genus Pisum.

13. The improvement of claim 12 wherein the plantlet regeneration culture is an aqueous suspension culture.

14. In a method for the morphogenetically competent development of cell cultures of a large-seeded legume, the improvement wherein morphogenesis in competent cell cultures is initiated by the coordinate change in auxin and nitrogen source in the culture medium.

15. The improvement according to claim 14 wherein somatic embryogenesis in competent cell cultures is initiated by the coordinate change in auxin activity level and nitrogen source.

16. The improvement according to claim 15 wherein the competent cell cultures are derived from the culturing of a large-seeded legume and the change in nitrogen source is a change from a culture medium wherein the only source of nitrogen for the culture is an ammonium salt, free of nitrate anion, to a culture medium wherein the source of nitrogen for the culture includes the nitrate anion.

* * * * *